US00PP21881P3

(12) United States Plant Patent
Patel

(10) Patent No.: US PP21,881 P3
(45) Date of Patent: Apr. 26, 2011

(54) BLUEBERRY PLANT NAMED 'HORTBLUE POPPINS'

(50) Latin Name: *Vaccinium corymbosum*
Varietal Denomination: Hortblue Poppins

(75) Inventor: Narandra Patel, Hamilton (NZ)

(73) Assignee: The New Zealand Institute for Plant and Food Research Limited, Auckland (NZ)

( * ) Notice: Subject to any disclaimer, the term of this patent is extended or adjusted under 35 U.S.C. 154(b) by 0 days.

(21) Appl. No.: 12/587,549

(22) Filed: Oct. 8, 2009

(65) Prior Publication Data

US 2010/0095414 P1 Apr. 15, 2010

Related U.S. Application Data

(60) Provisional application No. 61/195,636, filed on Oct. 9, 2008.

(51) Int. Cl.
*A01H 5/00* (2006.01)

(52) U.S. Cl. ..... Plt./157

(58) Field of Classification Search ..... Plt./157
See application file for complete search history.

(56) References Cited

U.S. PATENT DOCUMENTS

PP6,699 P 3/1989 Wood
PP6,700 P 3/1989 Wood

*Primary Examiner* — June Hwu
(74) *Attorney, Agent, or Firm* — Greenlee Sullivan P.C.

(57) ABSTRACT

A new and distinct variety of Northern Highbush blueberry plant is described. The variety results from selection among a population of seedlings derived from crossing the blueberry variety known as 'Nui' (U.S. Plant Pat. No. 6,699) and an unnamed seedling selection called 1386 (not patented). The fruit of this new variety has an attractive appearance characterised by outstanding fruit quality with a good bloom and good firmness; the plant has a characteristic upright habit, good architecture and attractive foliage. The new variety has been named 'Hortblue Poppins'.

7 Drawing Sheets

Genus and species of plant named: *Vaccinium corymbosum.*

Variety denomination: Hortblue Poppins

CROSS-REFERENCE TO RELATED APPLICATION

This application claims the benefit of U.S. Provisional Application No. 61/195,636, filed Oct. 9, 2008.

BACKGROUND OF THE INVENTION

The new variety was selected from a population of seedlings derived from crossing the blueberry varieties known as 'Nui' (seed parent) (U.S. Plant Pat. No. 6,699) and an unnamed seedling selection called 1386 (pollen parent) (not patented). The cross was made in 1988 and the new variety was selected in 1996 from among plants located on land at Ruakura, Hamilton, New Zealand, and was assigned the breeder code, B8.3.10. The new variety has since been named 'Hortblue Poppins'.

SUMMARY OF THE INVENTION

The fruit of this new variety has an attractive appearance characterised by outstanding fruit quality with a good bloom and good firmness; the plant has a characteristic upright habit, good architecture and attractive foliage. The new variety has been named 'Hortblue Poppins'.

The new variety is characterised as follows:

Maturity period: mid-season, generally from mid December in Ruakura, Hamilton, New Zealand, at a similar time to that of 'Bluecrop' (not patented). The new variety has also been tested in Germany (Hannover) where production occurs mid-season, generally during the third week of July, also similar to 'Bluecrop'.

Plant form and vigour: the plant is generally a medium size bush, with a characteristic upright habit, good architecture and attractive foliage. The leaf shape and habit are distinctive with the leaves turned inside and pointing upwards. The plant has medium to good vigour, similar to 'Bluecrop' and 'Duke' (not patented).

Yield: medium to low.

Berry size and shape: medium to small fruit, round to oblate berries, with good bloom, and firmness.

Colour: medium to light blue; blue black with bloom removed.

Fruit bloom: good intensity; attractive.

Pedicel scar: small.

Plant health: the plant does not seem to be susceptible to anthracnose (Colletotrichum acutatum).

BRIEF DESCRIPTION OF THE PHOTOGRAPHS

The accompanying photographs show typical specimens of the plant, foliage and fruit of the new variety as depicted in colors as nearly true as is reasonably possible to make the same in a color illustration of this character.

DETAILED DESCRIPTION

The observations, unless otherwise specified, were made in the 2007-2009 seasons on nine year old plants grown at Ruakura, Hamilton, New Zealand and additional information were collected from plants 12 year old growing in Germany during the summers 2008 and 2009. All dimensions in millimetres, weights in grams (unless otherwise stated). Colour terminology is in accordance with The Royal Horticultural Society Colour Charts 2001 edition.

Figure 1:
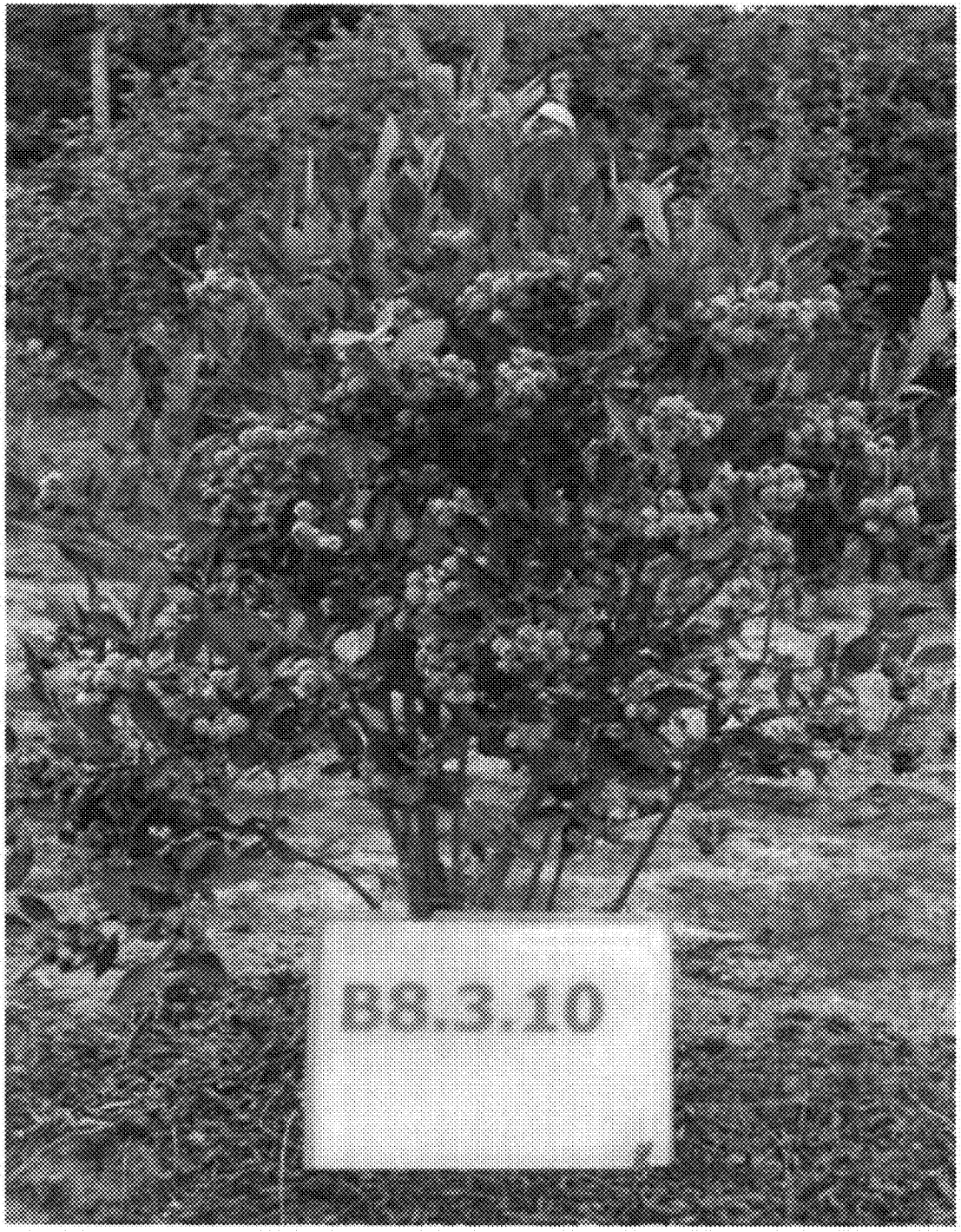
FIG. 1 shows a young, four year old, plant of 'Hortblue Poppins' and its distinctive upright habit, with its leaves turned inside and pointing upwards.
Figure 2:
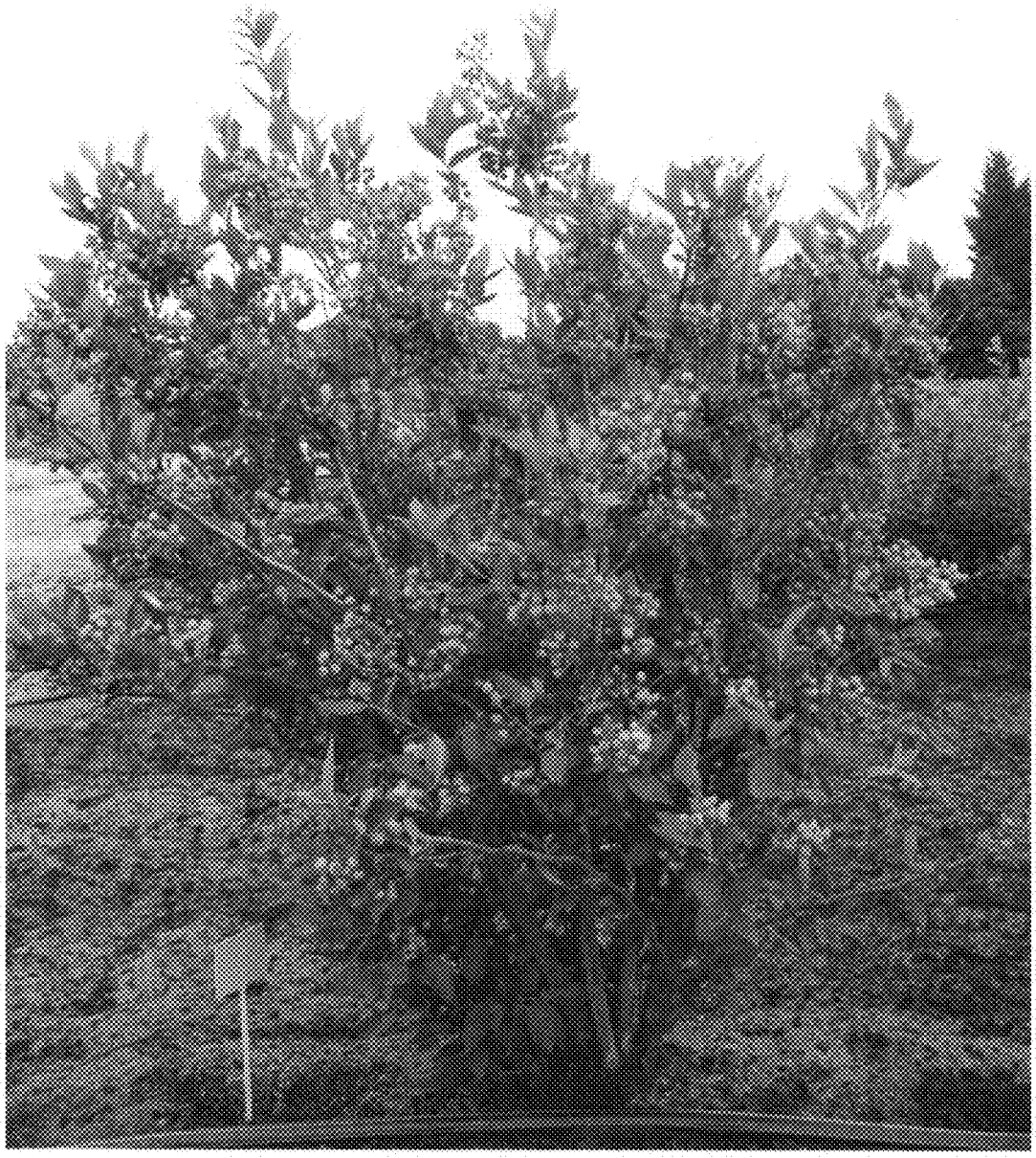
FIG. 2 shows typical adult, nine year old, plant of 'Hortblue Poppins' planted in the field.
Figure 3:
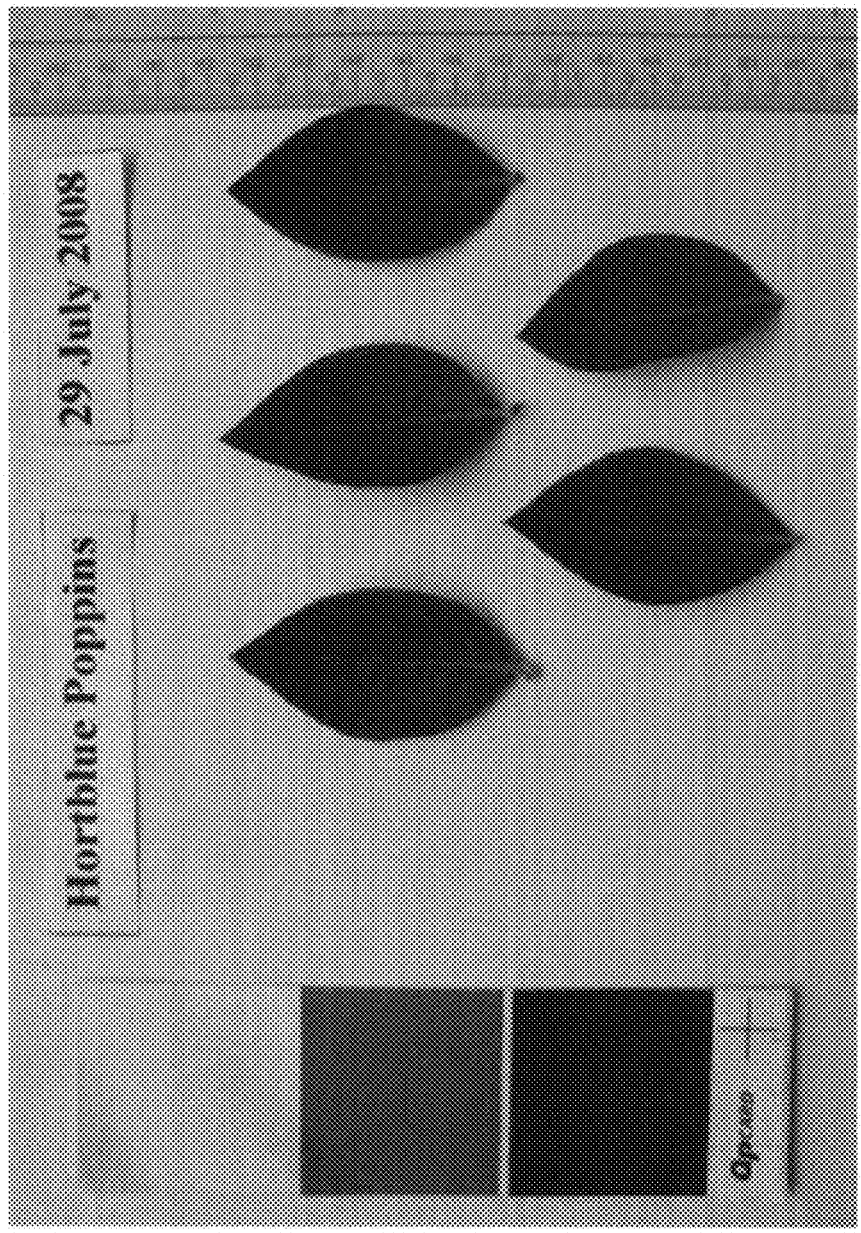
FIG. 3 shows the leaves of 'Hortblue Poppins' (grown in Germany).
Figure 4:
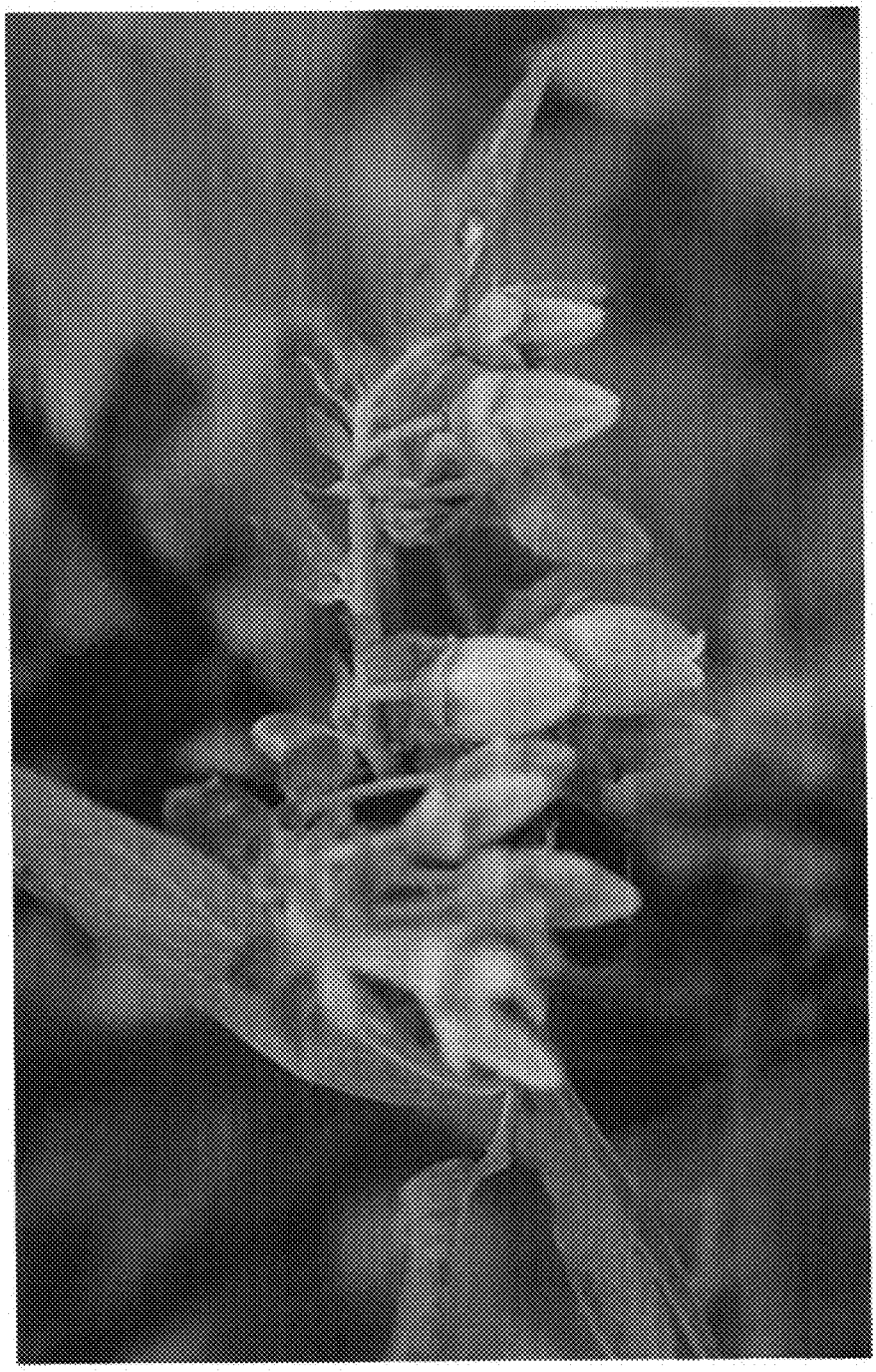
FIG. 4 shows the beginning of the flower opening of 'Hortblue Poppins' in Germany.
Figure 5:
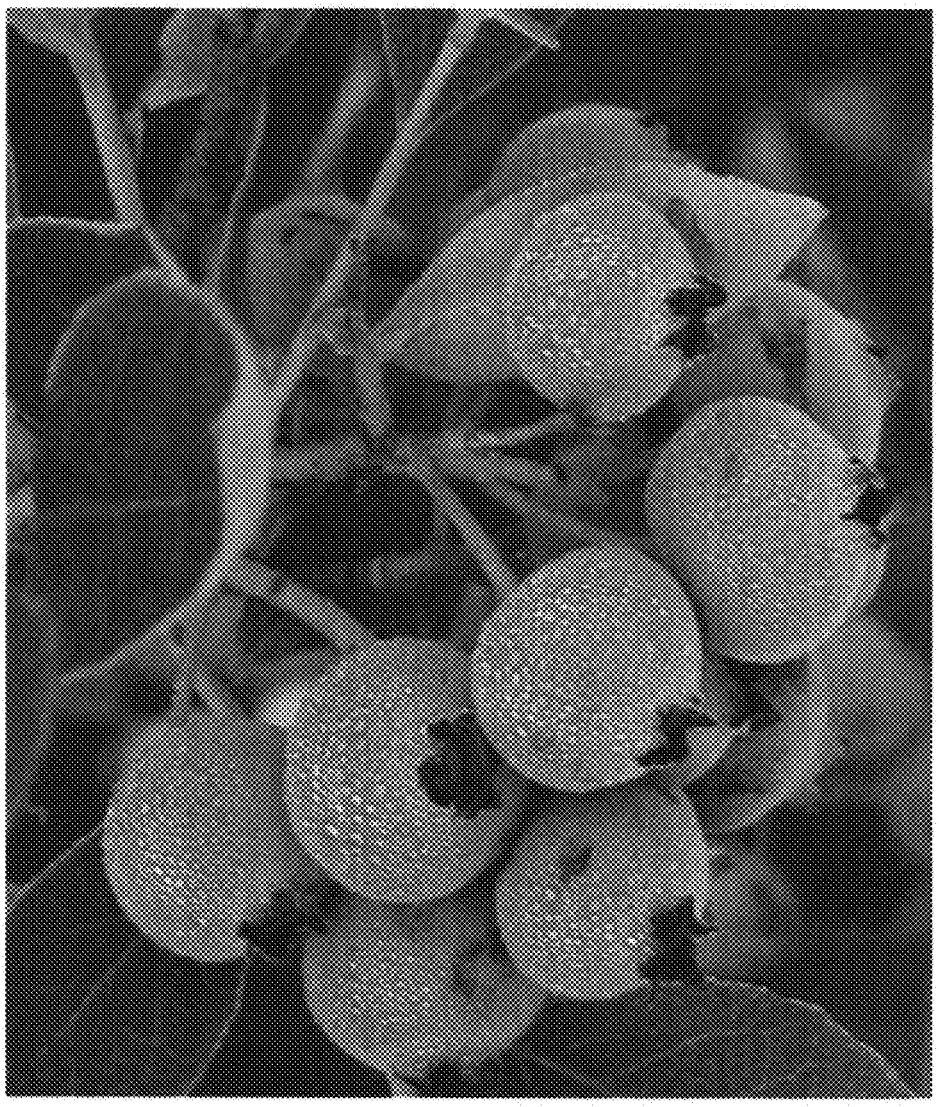
FIG. 5 shows the characteristic small, oblate to round fruit with good bloom of 'Hortblue Poppins'.
Figure 6:
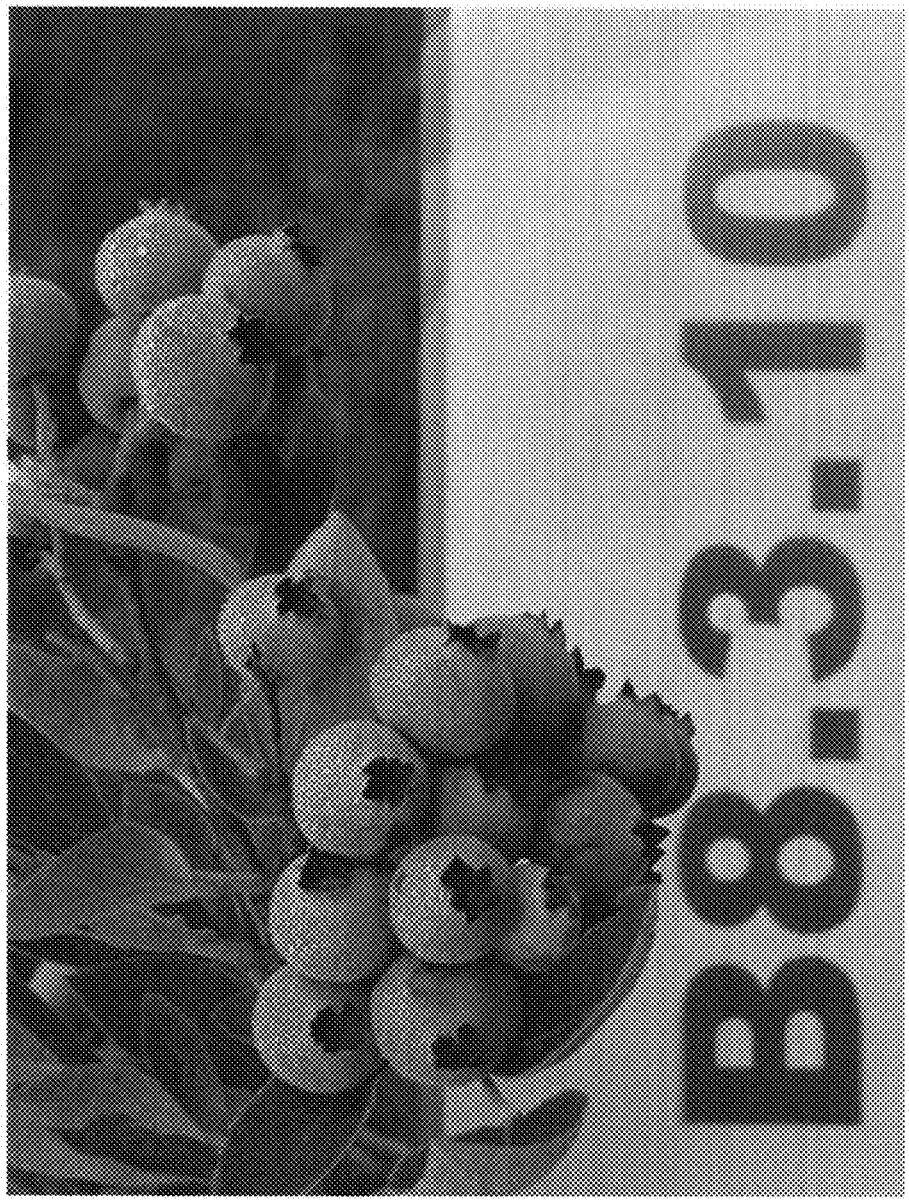
FIG. 6 shows the characteristic fruit cluster of 'Hortblue Poppins'.
Figure 7:
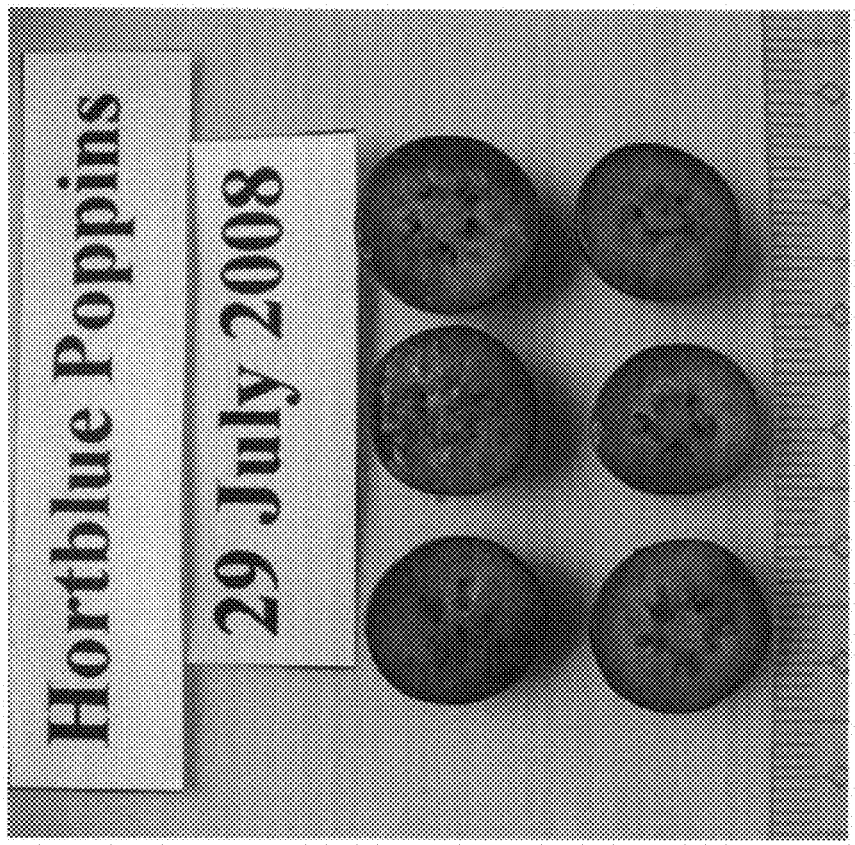
FIG. 7 shows the fruit sections of 'Hortblue Poppins', grown in Germany.
Figure 7:
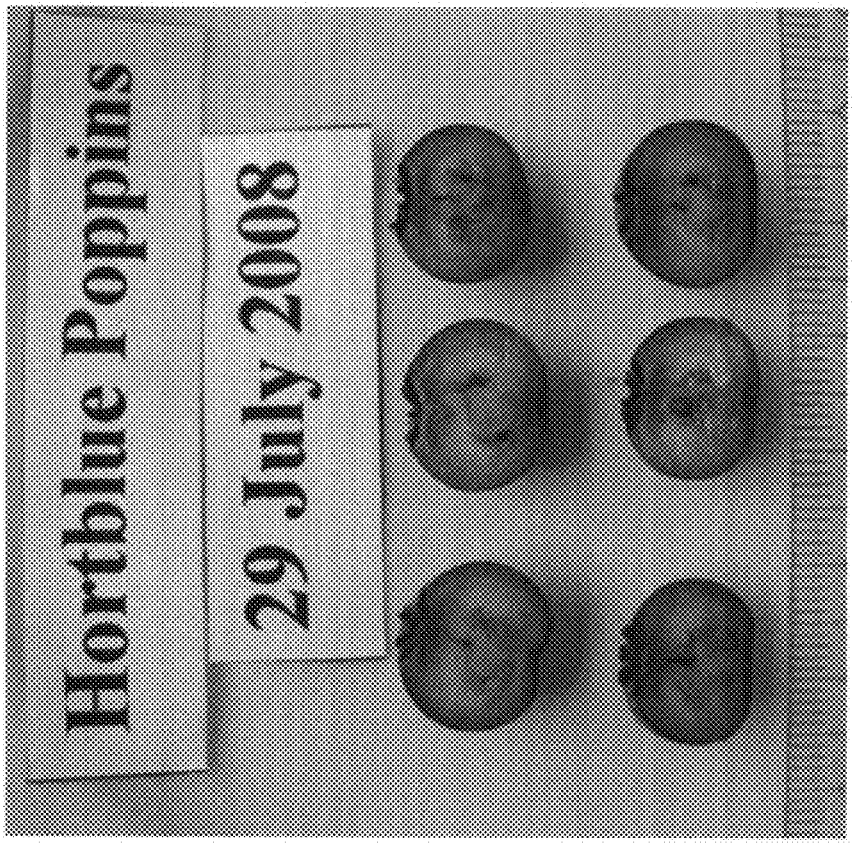

Plant and foliage:

This tetraploid plant is generally upright, and of medium vigour, similar to 'Bluecrop' and 'Duke'. The average height of a mature plant ranges from between 1.0 to 1.5 m with an average spread of between 0.8 and 1.2 m. These measurements are, however, dependent on a range of factors such as pruning practices and planting distances. The mature leaf is ovate in shape and typically averages 57 mm in length and approximately 28 mm in width, similar to the leaf size of plants of the variety 'Reka' (U.S. Plant Pat. No. 6,700) (63 mm in length and 36 mm in width) and smaller than those of 'Duke' (70 mm in length, 42 mm in width) and 'Nui' (80 mm in length, 50 mm in width). Generally the leaf margin has no serration, low glossiness on the upper surface, and no glaucescence on the upper surface.The base shape of the leaf ranges between acute and very shortly attenuate while the apex is typically best described as acuminate. Typically the petiole length averages 2.9 mm. The colour of the leaf is similar to 'Bluecrop'. The colouration of the upper leaf surface of 'Hortblue Poppins' is near Green 137A, while the lower leaf surface is near Green 138A. The vein and petiole colouration are near Yellow-green 152D, and the main vein and petiole also had a small amount of Red-purple 60B. The arrangement of leaves across the plant with individual leaves orientated with the upper surface turned towards the interior of the plant, and in a generally erect, upward, attitude contributes to the distinctive habit of the plant. This distinctive arrangement is visible in FIG. 1 and FIG. 2. The colour of mature wood is near Grey 201C while the colour of one year old wood is near Greyed-orange 166D This new variety has been asexually reproduced at Ruakura, Hamilton, New Zealand by soft wood cuttings.

Inflorescence:

The average number of flower buds per shoot is 10, with an observed range of 8-15. The estimation of number of buds per shoot was made on the fruiting (terminal) sections of shoots; this section typically averaging 19 cm in length.

Flowers are generally clustered and the width of the typical flower averages 7.7 mm, similar to 'Reka' and smaller than the parental plant 'Nui' averaging 10.3 mm. The corolla is urceolate in shape and has an average length of 9.3 mm, this is similar to 'Bluecrop' which as an average length of 9.1 mm but shorter than that of 'Nui' which has an average length of 11.3 mm. The colour of the petals on fully open mature flowers is near White 155A.

The flowers of 'Hortblue Poppins' consisted of ten stamens, this is consistent with other Northern Highbush blueberries such as 'Bluecrop' and 'Nui', along with one pistil. The average length of the stamens was 7.9 mm, and the average length of the pistil (including the style, stigma, and ovary) was, on average, 10.8 mm. There was insufficient pollen available for collection to gauge an accurate colour at this time.

The average length of the peduncle was 6.4 mm.

Self fertility of 'Hortblue Poppins' has not been tested. Recommended pollinators, based on alignment of flowering times, included 'Brigitta'(unpatented), 'Bluecrop', and 'Nui'.

Fruit:

'Hortblue Poppins' can be said to fruit on one year shoots only. However, there have been observations of flowering on current year shoots, this phenomenon should be considered an exception and is suggested to be due to environmental conditions. The fruit are of medium to small size, similar to 'Duke' under New Zealand growing conditions, averaging approximately 1.2 g. Observations indicate fruit size to be smaller than that of fruit of the parent 'Nui' (averaging 3.2g) and to comparative varieties such as 'Reka' (2.1g) and 'Bluecrop' (1.5g). Relatively similar comparative fruiting performance was observed under the growing conditions in Germany; 'Hortblue Poppins' having medium to small fruit (averaging 1.5 g), smaller than the parent 'Nui' (averaging 2.1g) and to the comparative varieties 'Reka' (1.7g) and 'Bluecrop' (1.9g). Generally, fruit is round to oblate in shape. Fruit diameter averages approximately 12.6 mm (observed range 10.7-14.4 mm) under New Zealand growing conditions and was slightly larger, the fruit diameter averaging 14.3 mm (within the range of 12.9-15.6), under the growing conditions in a different environment (Germany). Unripe fruit is green, within the range near Yellow—Green 144A to 144C. Ripe fruit has an attractive bloom. Fruit colour is light blue with the bloom intact, near Violet-Blue 98B, and skin colour when bloom is completely removed is near Blue 103A. The pedicel scar is very small, approximately 1.6 mm in diameter, similar to 'Duke' and 'Reka', and smaller than 'Bluecrop' (averaging 2.1 mm). The scar is generally dry. The fruit sweetness (Brix level) averages 12.4%, (observed range 11-14%) similar to 'Bluecrop' and 'Reka', and typically higher than 'Nui'. The fruit acidity measured as titratable acidity (%) averaged 0.36, similar to 'Duke' and less than 'Nui' (0.8%). Fruit is generally firm, giving a distinctive "crispness" when bitten. Fruit firmness averaged 240 g/mm (observed range 230-260 g/mm), firmer compared with fruit of the varieties 'Duke' (averaged 175 g/mm), 'Bluecrop' (averaged 166 g/mm), 'Reka' (averaged 168 g/mm) and 'Nui' (averaged 150 g/mm). Yield is medium to low, averaging approximately 1.2 kg (observed range 1-1.4 kg) per plant under German growing conditions. Seed size is approximately 2.5 mm with an average number of seeds per fruit of 17 (observed range approximately 14-22).

Events:

The time of vegetative bud burst observed in 2008 was the 11$^{th}$ September (New Zealand).

Time of beginning flowering recorded in New Zealand was similar to the vegetative bud burst around mid September and 50% of flowering occurred the 3$^{rd}$ October, about a week later than for 'Nui' and 'Duke' under the same growing conditions.

In Germany 'Hortblue Poppins' vegetative bud burst was observed as the $10^{th}$ April in 2009; 50% of flowering occurred $7^{th}$ May, similar to 'Nui' and about a week later than 'Bluecrop' and 'Duke'.

The fruit maturity period occurs in mid season and observations made in the 2007-2009 seasons indicated the fruit typically commenced ripening in the second week of December, at Ruakura (Hamilton), New Zealand, similar to 'Bluecrop'. In Germany fruit of 'Hortblue Poppins' commenced ripening in a similar period to 'Bluecrop', typically from the third week of July.

The main harvest period is generally mid season compared to other northern highbush varieties under the New Zealand and German growing conditions.

Disease and pests:

The plant does not seem to be susceptible to leaf rust (*Pucciniastrum vaccinii*) and to anthracnose fruit rot (*Colletotricum acutatum*). 'Hortblue Poppins' has no particular resistance or susceptibility to any common blueberry pests or insects.

Geographical adaptation:

Observations indicate that the variety performs well in the cool temperate climates of the Waikato region, New Zealand, and Hannover, Germany, under standard management practices for commercial blueberry production. The plant cold hardiness according to the American zone classification has not been determined.

Market use:

The market use for this plant and the fruit produced from this plant is for the home garden. However, the use of this plant for commercial plantings and its suitability for machine harvest is under investigation and once complete the market for fruit produced from this plant may be expanded dependent on the outcome.

The invention claim is:

1. A new and distinct variety of Northern Highbush blueberry plant, substantially as illustrated and described herein.

* * * * *